United States Patent [19]

Leach

[11] Patent Number: 5,232,443
[45] Date of Patent: Aug. 3, 1993

[54] COMBINED UROLOGICAL RETRACTOR AND INSTRUMENT FOR INSERTING SUPRAPUBIC CATHETER AND METHOD OF USE

[76] Inventor: Gary E. Leach, 2630 Winrow Ct., Rowland Heights, Calif. 91748

[21] Appl. No.: 915,907
[22] Filed: Jul. 17, 1992
[51] Int. Cl.⁵ ............................................. A61M 31/00
[52] U.S. Cl. ..................................... 604/54; 604/264; 606/198; 128/20
[58] Field of Search ............... 606/167, 170, 181, 191, 606/198, 205, 207, 208; 128/20, 4; 604/51, 54, 104–107, 109, 264, 272, 280

[56] References Cited

U.S. PATENT DOCUMENTS

| | | | |
|---|---|---|---|
| 832,201 | 10/1906 | Kistler | 606/198 X |
| 862,712 | 8/1907 | Collins | 606/198 X |
| 3,628,522 | 12/1971 | Kato | 606/180 X |
| 3,920,023 | 11/1975 | Dye et al. | 604/281 X |
| 5,133,727 | 7/1992 | Bales et al. | 606/170 |
| 5,152,749 | 10/1992 | Giesy et al. | 604/164 |

FOREIGN PATENT DOCUMENTS

| | | | |
|---|---|---|---|
| 368898 | 6/1963 | Switzerland | 606/191 |
| 736949 | 5/1980 | U.S.S.R. | 606/198 |

Primary Examiner—C. Fred Rosenbaum
Assistant Examiner—C. Maglione

[57] ABSTRACT

A urological instrument combining in itself a function of a prostate retractor and an instrument for the insertion of a suprapubic catheter. The instrument has a curved tubular body (10) inserted into which is a flexible metallic tubular catheter (32). The catheter (32) is moveable from a feed mechanism (24) and is pivotally connected to a pair of foldable jaws (40 and 42) located on the distal end of the instrument. When the catheter is shifted towards the proximal end of the instrument, the jaws (40 and 42) are opened and when the catheter is shifted towards the distal end, the jaws are folded and are used for the attachment of a bullet-like perforating cup (56). The catheter (32) has a leader (64). For use as an instrument for the insertion of a suprapubic catheter (104), the instrument is introduced into the patient's urinary bladder (14) and then is moved forward for perforating the anterior abdominal wall by pushing a leader (64) and then using this leader as a guide for directing the bullet-like perforating cup which expands the perforation channel. The instrument is then used as a conventional instrument for the insertion of a suprapubic catheter (104). In case the instrument is used as a retractor, the jaws are opened and form a lever for pulling the bladder neck and the prostate outward to a position more accesable for the urologist who performs an operation.

16 Claims, 4 Drawing Sheets

COMBINED UROLOGICAL RETRACTOR AND INSTRUMENT FOR INSERTING SUPRAPUBIC CATHETER AND METHOD OF USE

FIELD OF THE INVENTION

The present invention relates to urology, particularly to a combined urological retractor and instrument for inserting a suprapubic catheter. The invention also relates to a method of inserting a suprapubic catheter into the urinary bladder.

BACKGROUND OF THE INVENTION

In surgery, cystostomy is the formation of a fistulous opening and insertion into the urinary bladder and the placement of a drainage tube or a catheter into the urinary bladder through the fistulous opening. Placement of a suprapubic cystostomy tube is a common adjunct to surgery of the lower urinary tract such as prostatectomy, etc. Other than through open cystostomy, percutaneous insertion of the catheter frequently is done with a punch cystostomy kit.

A punch cystostomy kit, which also is known as a trocar, consists of a metal tube for guiding a pilot with a sharp end. The anterior abdominal wall is punched with the tube having the sharp end formed by the pilot and then the pilot is removed and replaced by a Foley catheter. Such a kit is described, e.g., in General Urology, D. R. Schmidt, II edition, 1984, pp. 141–144. The use of this kit is associated with complications including some serious complications such as placement of the catheter outside the bladder into the perivesical space or worse directly into a loop of bowel.

U.S. Pat. No. 3,640,281 issued February 1972 to Robertson describes a method and an instrument for inserting a suprapubic catheter into the bladder through the urinary tract. The instrument comprises a tube having a curved distal portion insertable through the urethra into the bladder to bring the distal end of the tube in engagement with the wall of the bladder in register with the suprapubic area of the abdominal wall. An incision is made through the abdominal wall and the wall of the bladder in register with the distal end of the instrument, which then emerges outwardly through the incision.

A disadvantage of this method is that it still requires a surgical intervention such as an incision of the anterior abdominal wall and that the incision required for this purpose has dimensions greater than those required for the insertion of the tube.

In some case, in particular, in the case of radical perineal prostatectomy, along with the insertion of a suprapubic tube it is necessary to use an instrument known as a retractor. A retractor is a surgical instrument for pulling back or retracting a prostate for placing it to the location more convenient and accessible for the operation. The retractor is usually an instrument having expandable ends which after insertion in a folded state can be unfolded to form projections perpendicular to the walls of the urinary bladder in the area of the urinary bladder neck, so that these projections can be used for moving the prostate gland and fixation thereof in the position more convenient for the operation. Thus, the perineal radical prostatectomy involves the use of two different instruments, i.e., a retractor and trocar. This makes the operation more complicated, long in time, and more susceptible to complications.

Furthermore, to reduce the risk of bowel injury, neither retractor nor trocar can be used as a device for filling the urinary bladder with a liquid or for inserting an optical fiber for viewing the operation site.

OBJECTS OF THE INVENTION

It is an object of the present invention to provide a urological instrument which combines in itself a retractor and a device for inserting a suprapubic catheter. Another object is to provide the above-mentioned instrument which is simple in construction, reliable in operation, reduces the risk of surgical complications, does not require a surgical incision, and can be used for filling the urinary bladder with the liquid or for inserting a optical fiber for viewing the operation cite.

BRIEF DESCRIPTION OF THE DRAWINGS

FIG. 3 is a longitudinal sectional view of the distal end of the instrument.

FIG. 4 is a view of a jaw opening/closing mechanism.

FIG. 5 is a fragmentary sectional view of the tool illustrating connection of a washing fluid valve.

DETAILED DESCRIPTION OF THE INSTRUMENT OF THE INVENTION

Figure 1:
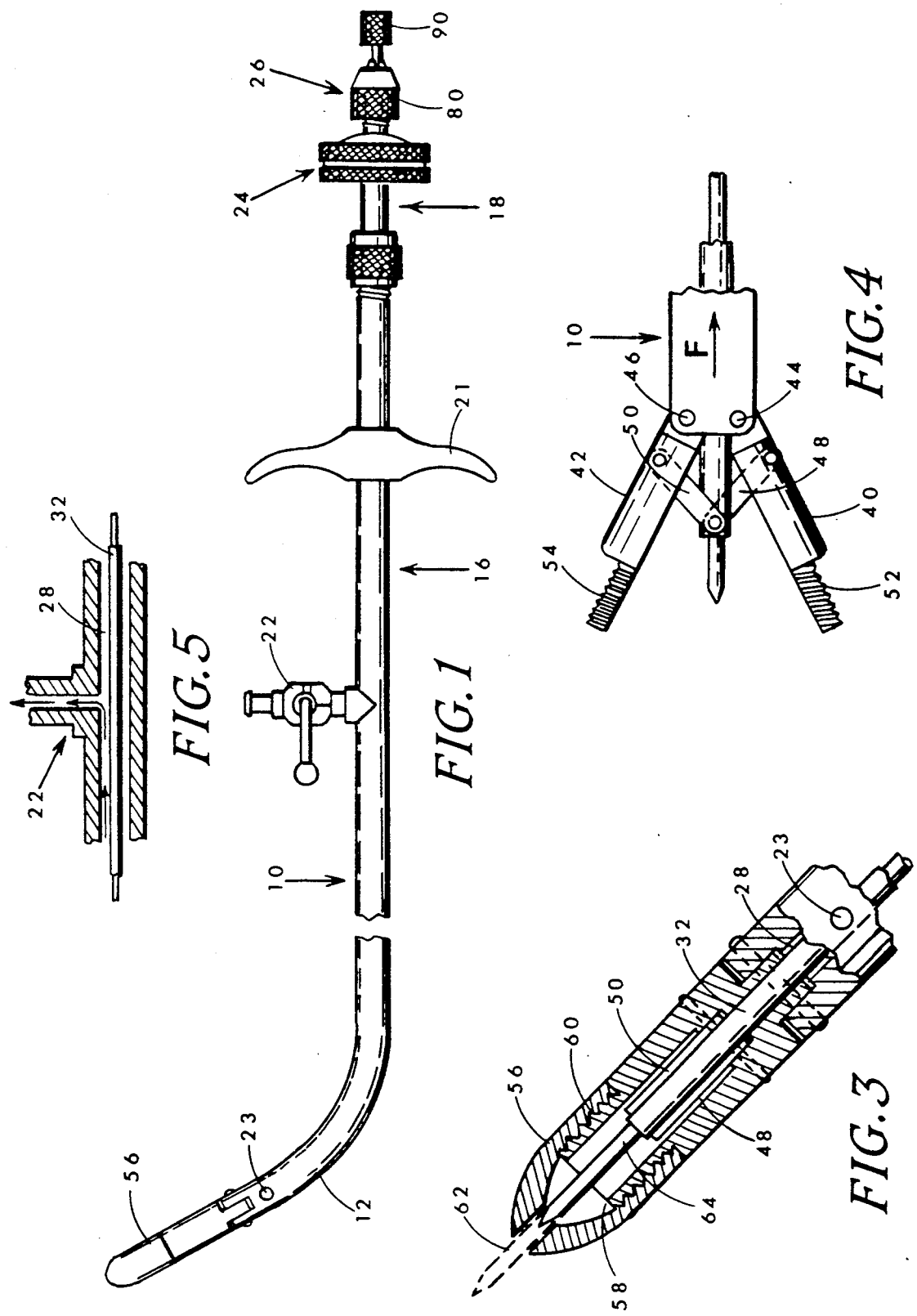
FIG. 1 is a general view of the instrument of the invention.

A general view of the instrument of the invention is shown in FIG. 1. The instrument has a hollow tubular body 10 made, e.g., of a stainless steel, with a curved distal portion 12 insertable through the urethra (not shown) into a urinary bladder 14 of a patient, a straight central portion 16, and a proximal portion 18 which is used for insertion of a pilot or a fiber optics (not shown). Central portion 16 has a handle 21 and a valve 22 for the supply of a liquid for washing bladder 14 or for the removal of the liquid from the bladder. Installed in proximal portion 18 of the instrument is a feed mechanism 24 and a fixation mechanism 26. Each part and mechanism of the instrument will be further described in a greater detail.

For the convenience of the description, we will call those ends of the parts and elements of the instrument which are close to the operator "proximal ends" and "proximal portions" and those parts which are remote from the operator "distal ends" and "distal portions".

Figure 2:
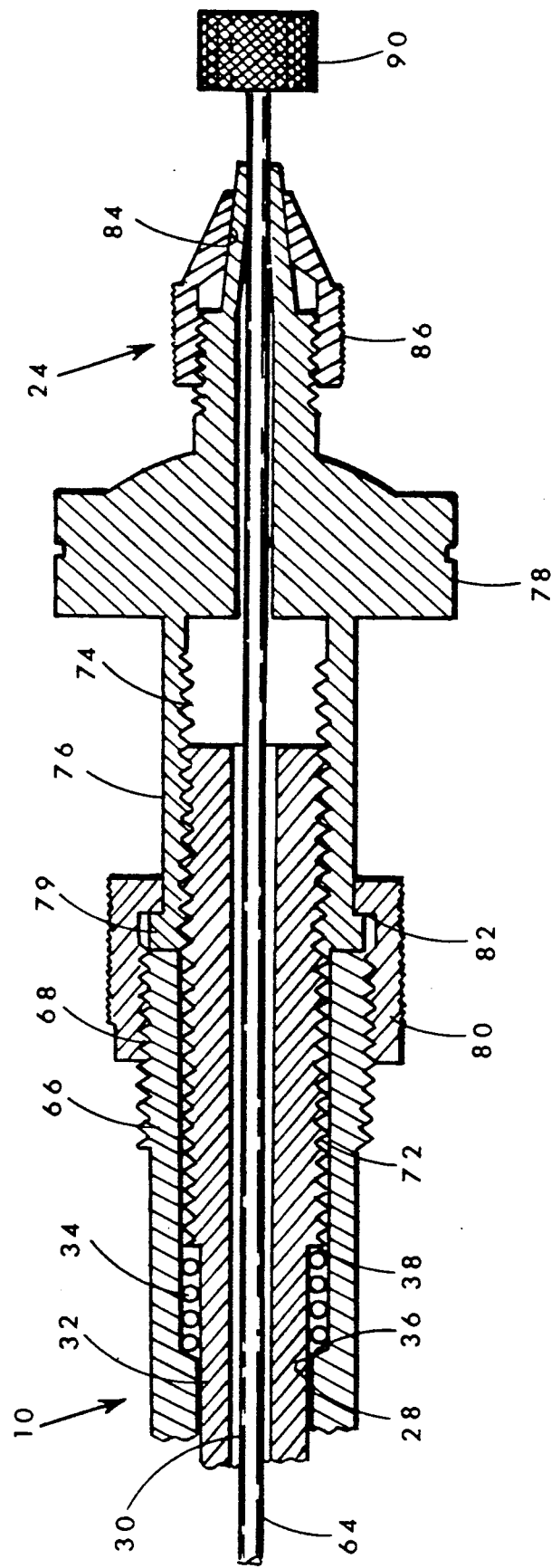
FIG. 2 is a longitudinal sectional view of the proximal end of the instrument.

As shown in FIG. 2, which is a longitudinal sectional view of a proximal part of the instrument, tubular body 10 has a central hole 28 which contains a flexible metallic tubular catheter 32. Tubular catheter 32 should be flexible enough to follow the curvature of distal portion 12 of the instrument. Catheter 32 can freely slide within body 10 and is spring-loaded within body 10 by means of a spring 34 located between an inner shoulder 36 of body 10 and an outer shoulder 38 of catheter 32.

At its distal end 12, which is shown in a longitudinal sectional view in FIG. 3, the instrument has movable jaws 40 and 42 which are pivotally connected at their proximal ends via pin 44 and 46, respectively, to the distal end of body 10. As shown in FIG. 4, which illustrates a mechanism used for opening and closing jaws 40 and 42, at their intermediate portions, jaws 40 and 42 are pivotally connected to tubular catheter 32 via links 48 and 50, respectively, so that sliding motions of catheter 32 within body 10 cause jaws 40 and 42 to open into position shown in FIG. 4, or close to a position shown in FIG. 3.

Jaws 40 and 42 have each a hollow semicylindrical configuration.

On their outer surfaces, jaws have external threads 52 and 54 which in a closed condition of the jaws shown in FIG. 3 together form a complete external threaded portion suitable for screwing onto it a bullet-like perforating cup 56. For this purpose, perforating cup 56 has a threaded hole 58 with an internal thread 60. Perforating cup has a bullet-like configuration and a central hole 62 for a pilot or filiform 64. Prior to the insertion into the patient's urethra (not shown), filiform 64, which is a metallic rod with a sharp end, is inserted into the instrument through its proximal end and passes through catheter 32 to a position shown in FIG. 3, i.e., within the limits of the instrument. The purpose and operation of filiform 64 will be described later in connection with operation of the instrument.

The proximal end of body 10 has a portion 66 (FIG. 2) of an increased diameter with an external thread 68. The proximal end of catheter which is located behind shoulder 38 also has an external thread 72 which engages an internal thread 74 of a feed sleeve 76. Feed sleeve 76 is an element of feed mechanism 24 and has a handle 78 for manually rotating this sleeve. On its distal end, feed sleeve 76 has a shoulder 79 of an enlarged diameter which is used as a stop for a nut 80. An inner shoulder 82 of nut 80 engages shoulder 79 of feed sleeve 76.

Inserted into the proximal end of feed sleeve 76 is a collet 87 which engages with an inner conical surface 84 of a nut 86. Nut 86 has a through hole 88, so that a flushing liquid tube 90 (or fiber optics [not shown]) can be inserted into catheter 32, pulled through it to the operation site, and fixed in the catheter by tightening nut 86.

Filling of the patent's bladder after insertion of the instrument and prior to the operation can be carried out through the central hole of catheter 32 and the filling fluid may be discharged through valve 22 in the direction of arrows shown in FIG. 5, which is a sectional view of the portion of the instrument where valve 22 is connected.

OPERATION OF THE RETRACTOR

Prior to the insertion into the patient's urethra (not shown), the instrument should have jaws 40 and 42 in the position shown in FIG. 3 with a perforating cup 56 screwed onto threads 52 and 54 of respective jaws. In this case, catheter 32 is shifted forward towards the distal end of the instrument, so that links 48 and 50 are folded, as shown in FIG. 3. Pilot 64 is hidden in catheter 32. It is understood that pilot 64 may be inserted into catheter 32 after the insertion of the instrument into the patient's bladder is completed. However, it is advantageous to have pilot 64 inside catheter 32 during the insertion of the instrument into the bladder, since the presence of the pilot will prevent dripping of urine to the outside through central hole of catheter 32.

Distal end 12 of the instrument is first inserted through the urethra (not shown) of the patient into urinary bladder 14. Suitable fluid, such as water, may be introduced into bladder 14 through flushing tube 90 inserted into catheter 32 and fixed in place by collet 82 tightened by nut 80 of fixation mechanism 26. Sterile fluid is instilled to the bladder through catheter 32 in a quantity sufficient to inflate or distend the bladder. This may be accomplished readily by connecting valve 22 to a fluid source (not shown). The waste fluid may be discharged from the urinary bladder through the central hole of catheter 32, from which pilot 64 has been preliminarily removed. If necessary, the washing fluid may be instilled into the patient's urinary bladder 14 through the central hole of catheter 32 and discharged from the patient's bladder through valve 22 (FIG. 5).

Figure 6:
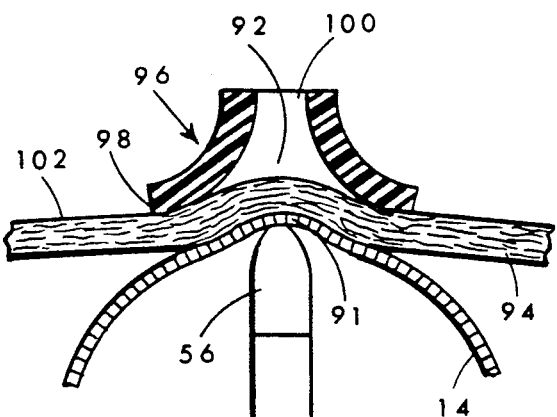
FIGS. 6 through 10 are sectional views showing sequential positions of the tool during the insertion of a suprapubic catheter.

Turning to FIG. 6, the next step is to bring closed distal end 12 of the instrument into engagement with the anterior wall 91 of urinary bladder 14 with sufficient force to provide a visible external protrusion 92 in the suprapubic region of an abdominal wall 94. This can be accomplished readily by suitable manipulation of the instrument from adjacent its proximal end 18.

Visible external protrusion 92 produced by the foregoing manipulations locates closed distal end 12 of the instrument very accurately. The zone of protrusion is further localized and limited by utilizing an external guide member 96 which is made in the form of a flanged body with a flange 98 with a central hole 100. Protrusion 92 is inserted into hole 100 and flange 98 is pressed to the outer surface 102 of abdominal wall 94. Pilot 64 having a sharp end is then shifted forward into the position shown by a broken line and reference numeral 64' in FIG. 3. Pilot 64 may be shifted forward manually through proximal end 18 of the instrument. In the protruded position, pilot 64 may be fixed by means of the fixation mechanism. For this purpose, nut 80 (FIG. 2) is loosened so that collet jaws 84 are expanded and allow the urologist to push flushing tube 90 forward. Nut 80 is then tightened, and flushing tube 90 is fixed in the protruded position shown in FIG. 3.

Figure 7:
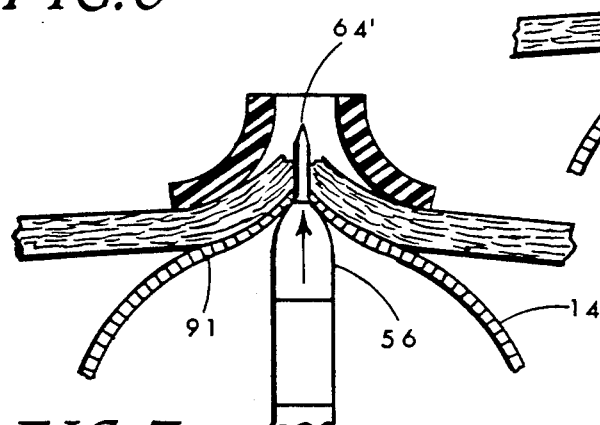
Figure 8:
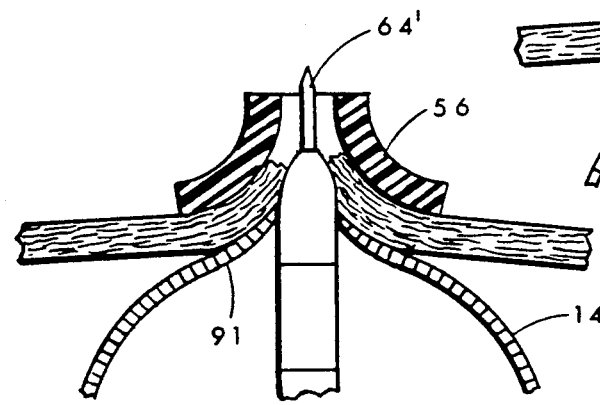

Perforation of the anterior abdominal wall may be carried out in two manners. According to one procedure, anterior abdominal wall 94 may be first perforated by pilot 64' alone with the instrument being stationary (FIG. 7). The instrument is then moved along pilot 64' as a guide and through the perforation made by pilot 64' (FIG. 8) so that the pilot hole made by pilot 64' is expanded by perforating cup 56. In this case, nut 80 (FIG. 2) must be loosened and collet jaws 84 must be released. According to the second procedure, pilot 64 is fixed in the instrument by means of fixation mechanism 26 and anterior abdominal wall is perforated by pilot together with perforating cup 56 as an integral unit (FIG. 8).

Figure 9:
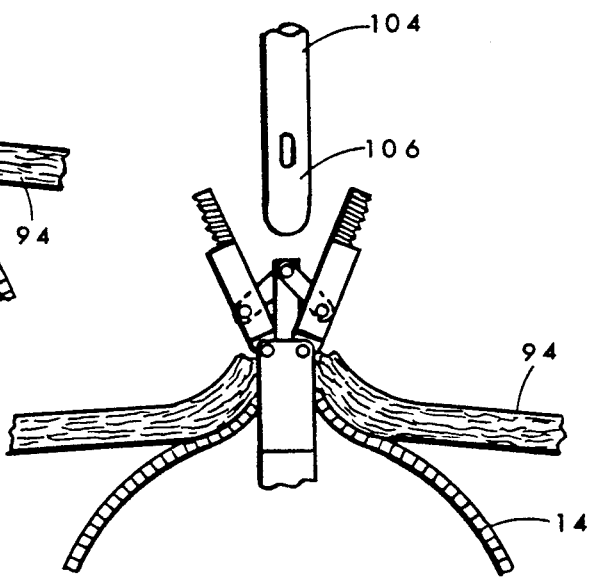
Figure 10:
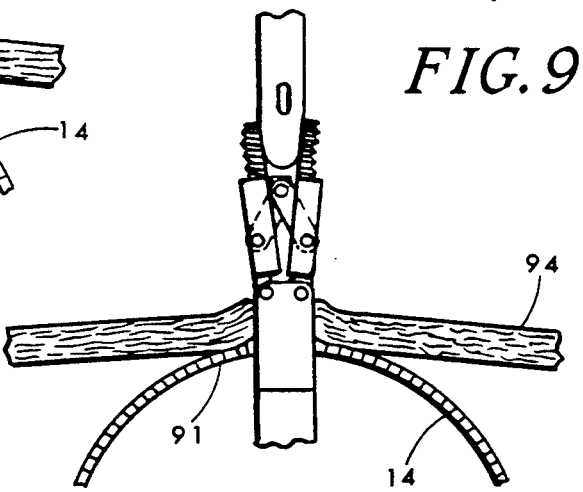

When distal end 12 of the instrument is outside of the patient's body, perforating cup 56 is untwisted from thread portions 52 and 54 of jaws 40 and 42 and removed. The urologist then rotates handle 78 of feed mechanism 24. As handle 78 is rotated (FIG. 2), its internal thread 74 engages external thread 72. As shoulder 79 of handle 78 may only rotate and is limited against axial movement by threaded portion 66 of body 10 and inner shoulder 82 of nut 80, catheter 32 begins to move axially toward the proximal end of the instrument. As catheter 32 moves in the above-mentioned direction, which is shown by arrow F in FIG. 4, jaws 49 and 42 are moved outward pivoting around their pins 44 and 46 through links 48 and 50. This movement is continued until they open the space sufficient for the insertion of a suprapubic catheter (FIG. 9) such as a Foley catheter 104, and at least the tip portion thereof 106 is inserted into distal end 12 of the instrument. Next the urologist clamps the inserted end of Foley catheter 104 in the instrument by reversing rotation of handle 78, so that catheter 32 is shifted in the direction opposite the one shown by arrow F. As a result, Foley catheter 104 is firmly clamped in the instrument between jaws 40 and 42 (FIG. 10).

The urologist then pulls the instrument together with Foley catheter 104 into the urinary bladder 14. After the Foley catheter has been inserted to the proper extent, jaws 40 and 42 are slightly opened in the same manner as described above and the instrument of the invention is removed from the bladder. An inflatable portion 110 of Foley catheter 104 is inflated in a conventional manner known in the art. The inflated portion then retains tip portion 106 within the bladder.

If necessary, with pilot 64 removed the central opening of catheter 32 may be use for the insertion of fiber optics for examination of the urinary bladder.

If the patient is a female, after the insertion of the Foley catheter, the instrument is removed.

Figure 11:
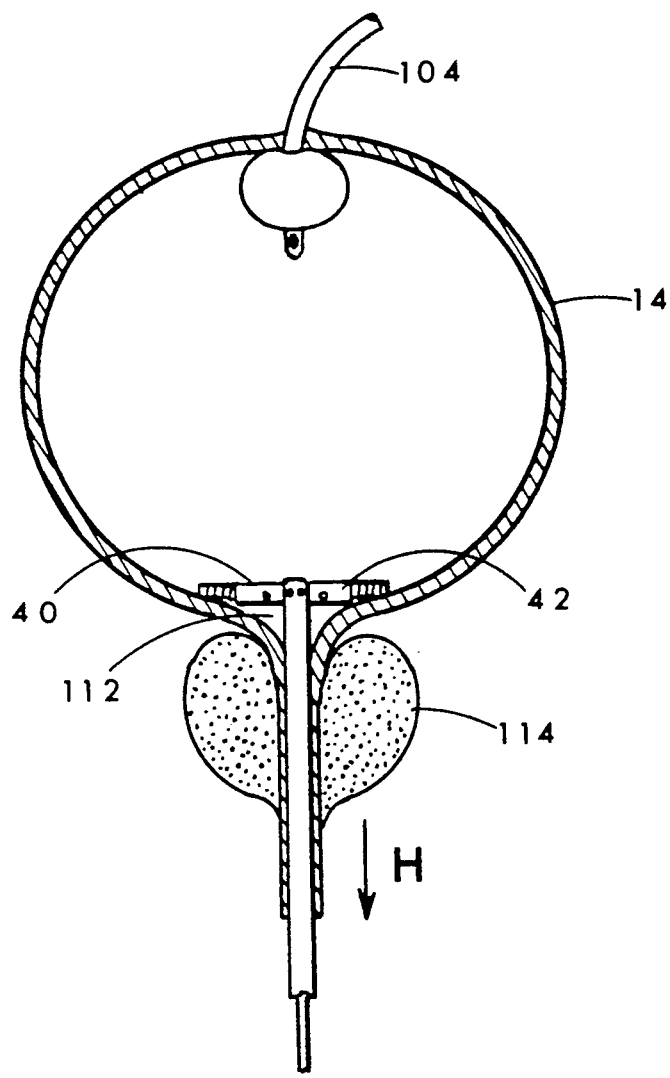
FIG. 11 is a sectional view illustrating the use of the instrument of the invention as a retractor used for perineal prostatectomy or a similar operation.

In case of a male patient with a prostatic cancer requiring surgery, such as perineal prostatectomy, as shown in FIG. 11, without removal of the instrument from urinary bladder 14 after the insertion and fixation of Foley catheter 104, jaws 40 and 42 can be opened to full extent or for about 90°, and then the instrument can be pulled in the direction of the urinary bladder neck 112. As a result, the bladder neck and a prostate 114 are pulled outward in the direction of an arrow H. This makes prostate 114 more accessible for the urologist to perform perineal prostatectomy.

SUMMARY, RAMIFICATIONS, SCOPE

Thus it has been shown that the invention provides a urological instrument which combines in itself a retractor and a device for inserting a suprapubic catheter. The above-mentioned instrument is simple in construction, reliable in operation, reduces the risk of surgical complications, does not require a surgical incision, and can be used for filling the urinary bladder with the liquid or for inserting a optical fiber for viewing the operation cite. The instrument is universal and is suitable for internal cystoscopy, as well as for retracting the prostate to facilitate perineal prostatectomy. It also allows insertion of fiber optics for the observation of the operation site.

Although the instrument was shown and described in the form of one specific embodiment, this embodiment, its parts, materials, and configurations have been given only as examples, and many other modifications of the instrument are possible. For example, the jaws may have different configuration and may be pivotally connected to the catheter through a different mechanism. The jaws may be opened from a different feed mechanism, and the pilot may be locked by a screw rather than by a collet device. The instrument as a retractor may be used not only in male patients for perineal prostatectomy but in female patients to facilitate any operation which must be carried out in the perineal area. Therefore, the scope of the invention should be determined not only by the example given, but by the appended claims and their legal equivalents.

I claim:

1. A method of inserting a suprapubic catheter, characterized by the use of an instrument having a cylindrical body with a curved distal portion terminating in a tubular distal end provided with a removable closure and having a through central hole, a straight proximal portion, a first flexible catheter having a distal end, a proximal end, and a central hole and inserted into said through central hole of said body, and jaws pivotally connected to a distal portion of said catheter, said method comprising the steps of:

inserting said distal portion of said instrument through the urethra into the urinary bladder of a patient and into engagement with the anterior wall of the urinary bladder in register with the suprapubic area of said abdominal wall;

displacing said distal end of said instrument outwardly to the extent that the abdominal walls are perforated and said closure protrudes outwardly;

removing said closure from said distal end of said instrument;

opening said jaws by pivoting them outwardly from each other so that a space sufficient for inserting a second catheter is formed;

inserting a portion of said second catheter into said space;

closing said jaws by pivoting them towards each other until said second catheter is fixed in said instrument;

displacing said distal end of said instrument into the urinary bladder through said perforation; and withdrawing said instrument from the urinary bladder through the urethra, leaving a portion of said second catheter within the urinary bladder.

2. The method of claim 1 wherein said instrument being further provided with a pilot having a sharpened end and insertable into said central hole of said first catheter prior to perforating the abdominal walls.

3. The method of claim 2 wherein said proximal portion of said instrument body has a feed mechanism for displacing said first catheter with respect to said body for opening and closing said jaws.

4. The method of claim 1 wherein said instrument being further provided with an external guide means for localization of the zone of perforation of the anterior wall of the urinary bladder, said external guide means being placed onto the patient's body above said zone of perforation prior to perforation of said anterior wall.

5. The method of claim 1, further including a step of supplying a fluid into the urinary bladder through said central hole of said first catheter after inserting said instrument into the urinary bladder and prior to inserting said pilot.

6. A method of inserting a suprapubic catheter, characterized by the use of an instrument having a cylindrical body with a curved distal portion terminating in a tubular distal end provided with a removable closure and having a through central hole, a straight proximal portion, a first flexible catheter having a distal end, a proximal end, and a central hole and inserted into said through central hole of said body, jaws pivotally connected to a distal portion of said catheter, and a pilot with a sharpened distal end insertable into said central hole of said first catheter through its proximal end and capable of protruding to the outside of said instrument through said distal end of said first catheter, said method comprising the steps of:

inserting said distal portion of said instrument through the urethra into the urinary bladder of a patient and into engagement with the anterior wall of the urinary bladder in register with the suprapubic area of said abdominal wall;

inserting said pilot into said central hole of said first catheter and perforating the anterior wall of the urinary bladder with said sharpened end of said pilot to the extent that said pilot makes a perforation in said anterior wall and protrudes outwardly therethrough;

displacing said distal end of said instrument outwardly through said perforation;

removing said closure from said distal end of said instrument;

opening said jaws by pivoting them outwardly from each other so that a space sufficient for inserting a second catheter is formed;

inserting a portion of said second catheter into said space;

closing said jaws by pivoting them towards each other until said second catheter is fixed in said instrument;

displacing said distal end of said instrument into the urinary bladder through said perforation; and withdrawing said instrument from the urinary bladder through the urethra, leaving a portion 7. The method of claim 6 wherein said distal portion of said instrument body has a feed mechanism for displacing said first catheter with respect to said body for opening and closing said jaws.

8. The method of claim 6 wherein said instrument being further provided with an external guide means for localization of the zone of perforation of the anterior wall of the urinary bladder, said external guide means being placed onto the patient's body above said zone of perforation prior to perforation of said anterior wall.

9. The method of claim 8, further including a step of supplying a fluid into the urinary bladder through said central hole of said first catheter after inserting said instrument into the urinary bladder and prior to inserting said pilot.

10. A method of inserting a suprapubic catheter, characterized by the use of an instrument having a cylindrical body with a curved distal portion terminating in a tubular distal end provided with a removable closure and having a through central hole, a straight proximal portion, a first flexible catheter having a distal end, a proximal end, and a central hole and inserted into said through central hole of said body, jaws pivotally connected to a distal portion of said catheter, a pilot with a sharpened distal end insertable into said central hole of said first catheter through its proximal end and capable of protruding to the outside of said instrument through said distal end of said first catheter, a locking mechanism for locking said pilot or any longitudinal element insertable into said through central hole of said first catheter, said method comprising the steps of:

inserting said distal portion of said instrument through the urethra into the urinary bladder of a patient and into engagement with the anterior wall of the urinary bladder in register with the suprapubic area of said abdominal wall;

supplying a fluid into the bladder said through central hole of said first catheter for filling the urinary bladder;

inserting said pilot into said central hole of said first catheter and perforating the anterior wall of the urinary bladder with said sharpened end of said pilot to the extent that said pilot makes a perforation in said anterior wall and protrudes outwardly therethrough;

locking said pilot in said instrument in said protruding position thereof;

perforating the anterior wall of the urinary bladder with said sharpened end of said pilot and then with said distal end of said body to the extent that said pilot and then said distal end of said body make a perforation in the anterior wall and protrude outwardly therethrough; displacing said distal end of said instrument outwardly through said perforation;

removing said closure from said distal end of said instrument;

opening said jaws by pivoting them outwardly from each other so that a space sufficient for inserting a second catheter is formed;

inserting a portion of said second catheter into said space;

closing said jaws by pivoting them towards each other until said second catheter is fixed in said instrument;

displacing said distal end of said instrument into the urinary bladder through said perforation; and withdrawing said instrument from the urinary bladder through the urethra, leaving a portion of said second catheter within the urinary bladder.

11. The method of claim 10 wherein said second catheter is a Foley catheter.

12. A method of inserting a suprapubic catheter with the use of an instrument which is then used as a urological retractor facilitating operation in the area of perineum, said instrument having a cylindrical body with a curved distal portion terminating in a tubular distal end provided with a removable closure and having a through central hole, a straight proximal portion, a first flexible catheter having a distal end, a proximal end, and a central hole and inserted into said through central hole of said body, and jaws pivotally connected to a distal portion of said catheter, said method comprising the steps of:

inserting said distal portion of said instrument through the urethra into the urinary bladder of a patient and into engagement with the anterior wall of the urinary bladder in register with the suprapubic area of said abdominal wall;

displacing said distal end of said instrument outwardly to the extent that the abdominal walls are perforated and said closure protrudes outwardly;

removing said closure from said distal end of said instrument;

opening said jaws by pivoting them outwardly from each other so that a space sufficient for inserting a second catheter is formed;

inserting a portion of said second catheter into said space;

closing said jaws by pivoting them towards each other until said second catheter is fixed in said instrument;

displacing said distal end of said instrument into the urinary bladder through said perforation;

opening said jaws to positions substantially perpendicular to said distal portion of said cylindrical body of said instrument;

moving said instrument toward a bladder neck of said urinary bladder until said jaws come in contact with said urinary bladder neck; and pulling said instrument in the direction of the urethra by applying a force from said jaws to said urinary bladder neck, so that said urinary bladder neck is retracted toward said perineum.

13. A combined urological retractor and instrument for inserting a suprapubic catheter comprising:
- a cylindrical body having a curved distal portion and a straight proximal portion, said cylindrical body having a through hole;
- a pair of jaws pivotally attached to the end of said distal portion;
- flexible catheter having a distal end, a proximal end, and a central hole, said flexible catheter being slidingly inserted into said through hole of said cylindrical body, said jaws being kinematically connected to said distal end of said catheter through pivotal links so that movement of said catheter with respect to said cylindrical body opens or closes said jaws, said jaws having outer thread on their peripheries, said jaws having a semicylindrical configuration which in a closed state of said jaws form a cylinder with a central opening;
- a removable cover of a bullet-like configuration which has an internal thread engageable with said outer thread of said jaws when said jaws are in their closed state, so that said removable cover can be threaded onto said jaws or untwisted therefrom, said removable cover has a hole in its distal end;
- a pilot with a sharpened distal end insertable into said central hole of said catheter through said proximal end thereof and capable of protruding to the outside of said instrument through said distal end of said catheter and in communication with said proximal end of said catheter;
- a locking mechanism for locking said pilot or any longitudinal element insertable into said central hole of said catheter; and
- a feed mechanism for moving said catheter with respect to said cylindrical body.

14. The instrument of claim 13 wherein said feed mechanism comprises a an outer thread on said proximal end of said catheter, a rotating body having an inner thread engaged with said outer thread of said catheter, and means for restricting said rotating body against axial movement with respect to said catheter, but allowing rotation with respect thereto, so that when said rotating body rotates without axial movement, said catheter is moved axially and its movement opens or closes said jaws.

15. The instrument of claim 14 wherein said locking mechanism is installed on said rotating body and engages said pilot so that said pilot can be locked with respect to said rotating body in a selected position, said hole in said distal end of said removable cover having a diameter greater than an outer diameter of said pilot so that said pilot can pass through said hole.

16. The instrument of claim 15, further including a valve for the supply or removal of flushing liquid through said instrument to the urinary bladder or therefrom, said valve being connected to said through hole of said cylindrical body.

* * * * *